United States Patent [19]
Zepp et al.

[11] Patent Number: 5,663,043
[45] Date of Patent: Sep. 2, 1997

[54] METHOD FOR INACTIVATING NON-ENVELOPED VIRUSES USING A VIRICIDE-POTENTIATING AGENT WITH A PHOTOACTIVATIBLE VIRUCIDE

[75] Inventors: Charles M. Zepp, Hardwick; Donald L. Heefner, Hudson, both of Mass.

[73] Assignee: Hemasure Inc., Marlborough, Mass.

[21] Appl. No.: 368,780

[22] Filed: Jan. 4, 1995

[51] Int. Cl.$^6$ ............................... A01N 1/02; C12N 7/06
[52] U.S. Cl. ............................... 435/2; 435/236; 435/238
[58] Field of Search ............................... 435/2, 236, 238

[56] References Cited

U.S. PATENT DOCUMENTS

| | | | |
|---|---|---|---|
| 4,169,204 | 9/1979 | Hearst et al. | 546/270 |
| 4,294,822 | 10/1981 | Kaufman | 424/59 |
| 4,328,239 | 5/1982 | Kaufman | 424/279 |
| 5,288,605 | 2/1994 | Lin et al. | 435/902 |

OTHER PUBLICATIONS

Suomela, "Inactivation of Viruses in Blood and Plasma Products," Transfusion Medicine Reviews, vol. VII, No. 1, 42–57 (Jan. 1993).
Burnouf–Radosevich et al., "A Pasteurized Therapeutic Plasma," Infusionstherapie, 19:91–4 (1992).
Hellstern et al., "Manufacture and in vitro Characterization of a Solvent/Detergent–Treated Human Plasma," Vox Sang, 63:178–85 (1992).
Piquet et al., "Virus Inactivation of Fresh Frozen Plasma by a Solvent Detergent Procedure: Biological Results", Vox Sang, 63:251–6 (1992).
Horowitz et al., "Solvent/Detergent–Treated Plasma: A Virus–Inactivated Subst. for Fresh Frozen Plasma", Blood, 79(3):826–31 (Feb. 1, 1992).
Mohr et al., "No evidence for neoantigens in human plasma after photo–chemical virus inactivation," Ann. Hematol., 65:224–8 (1992).
Parsons, "Psoralen Photochemistry," Photochemistry and Photobiology, 32:813–21 (1980).
Anderson et al., "Psoralen Photochemotherapy of Cutaneous Disorders," Ann. Rev. Pharmacol. Toxicol., 20:235–57 (1980).
Wieding et al., "Fresh–Frozen–Plasma," Infusionstherapie, 19:84–90 (1992).
Wagner et al., "Differential sensitivities of viruses in red cell suspensions to methylene blue photosens.," Transfusion, 34(6):521–6, 1994.
Wagner et al., "Red cell alterations associated with virucidal methylene blue phototreatment," Transfusion, 33:30–6 (1993).
BioWorld Today, vol. 4, No. 229, pp. 1 and 4 (Nov. 24, 1993).
Lambrecht et al., "Photoinact. of Viruses in Human Fresh Plasma by Phenothiaz. Dyes in Comb. with Vis. Light," Vox Sang, 60:207–13, 1991.
Goodrich et al., "Selective inact. of viruses in the presence of human platelets: UV sensit. with psoralen deriv.," Proc. Natl. Acad. Sci. USA, 91:5552–6 (Jun. 1994).

Letsinger et al., "Cholesteryl–conjugated oligonuc: Synth., proper., and activity as inhibitors of replic. of human immunodef. virus in cell culture", Proc. Natl. Acad. Sci. USA, 86:6553–6 (Sep. 1989).
Asseline et al., "Nucl. acid–binding molec. with high aff. and base seq. specificity: Intercal. agents coval. linked to oligodeoxynucl.," Proc. Natl. Acad. Sci. USA, 81:3297–301 (Jun. 1984).
Barthel et al., "Gene Transfer Optimization with Lipospermine–Coated DNA," DNA and Cell Biology, 12(6):553–60 (1993).
Loeffler et al., "Lipopolyamine–Mediated Transfection Allows Gene Exp. Stud. in Primary Neuronal Cells," J. Neurochem., 54:1812–5 (1990).
Promega Technical Bulletin No. 116 entitled "Transfectam Reagent for the Transfection of Eukaryotic Cells," (Jul. 1994).
Technical literature produced by Life Technologies, Inc. regarding its LipofectAMINE Reagent (Jan. 27, 1994).
Technical literature produced by Boehringer Mannheim GmbH regarding its transfection reagent (DOTAP) (No pub. date).
Letsinger et al., "Cholesteryl–conjugated oligonucleotides: Synthesis, properties, and activity as inhibitors of replication of human immunodeficiency virus in cell culture," PNAS USA, 1989; 86:6553–6.
Bowler et al., "Synthesis and DNA Binding and Photonicking Properties of Acridine Orange Linked by a Polymethylene Tether to (1,2–Diaminoethane)dichloroplatinum(II)," J. Am. Chem. Soc., 1984; 106:6102–4.
Krotz et al., "Assembly of DNA Recognition Elements on an Octahedral Rhodium Intercalator: Predictive Recognition of 5'–TGCA–3' by $\Delta$–[Rh[(R,R)–Me$_2$trien]phi]$^{3+}$", J. Am. Chem. Soc., 1993; 115:12577–8.

(List continued on next page.)

*Primary Examiner*—David M. Naff
*Assistant Examiner*—S. Saucier
*Attorney, Agent, or Firm*—Kriegsman & Kriegsman

[57] ABSTRACT

Method for inactivating non-enveloped viruses using a viricide-potentiating agent. In a preferred embodiment, the method may be used to inactivate non-enveloped viruses present within a sample of whole blood or a blood product and comprises (a) adding to the blood sample a photoactivatable viricide, such as a psoralen, hypericin, methylene blue, toluidine blue or the like, which, when activated, is effective in inactivating enveloped viruses; (b) adding to the blood sample a viricide-potentiating chemical agent that increases the sensitivity of non-enveloped viruses to the activated viricide; and (c) activating the photoactivatable viricide. Preferably, the viricide-potentiating chemical agent includes a first moiety which possesses an affinity for a component of the non-enveloped virus and a second moiety which includes a lipid tail, the first and second moieties being structurally interrelated so that, when the first moiety becomes associated with a component of the non-enveloped virus, the second moiety penetrates or at least partially surrounds the viral capsid of the non-enveloped virus. Examples of the chemical agent include cationic lipopolyamines, such as dioctadecylamidoglycylspermine.

19 Claims, 1 Drawing Sheet

OTHER PUBLICATIONS

Wagner et al., "DNA–Binding Transferrin Conjugates as Functional Gene–Delivery Agents: Synthesis by Linkage of Polylysine or Ethidium Homodimer to the Transferrin Carbohydrate Moiety," Bioconjugate Chem., 1991; 2:226–31.

Asseline et al., "Oligodeoxynucleotides covalently linked to intercalating dyes as base sequence–specific ligands. Influence of dye attachment site," The EMBO Journal, 1984; 3(4):795–800.

Verspieren et al., "An acridine–linked oligodeoxynucleotide targeted to the common 5' end of trypanosome mRNAs kills cultured parasites," Gene, 1987; 61:307–15.

Helene et al., "Oligodeoxynucleotides covalently linked to intercalating agents: a new class of gene regulatory substance," Biochimie, 1985; 67:777–83.

Thuong et al., "Solid–phase synthesis of Oligo–α–and Oligo–β–deoxynucleotides Covalently Linked to an acridine," Tetrahedron Letters, 1988; 29(46):5905–8.

Asseline et al., "Nucleic acid–binding molecules with high affinity and base sequence specificity: Intercalating agents covalently linked to oligodeoxynucleotides," PNAS USA, 1984; 81:3297–301.

Magno et al., "Carbomethoxy–derivatives of Psoralen: Interactions with DNA and Photobiological Properties," Farmaco. Ed. Sci., 1981; 36(7):629–47.

METHOD FOR INACTIVATING NON-ENVELOPED VIRUSES USING A VIRICIDE-POTENTIATING AGENT WITH A PHOTOACTIVATIBLE VIRUCIDE

FIELD OF THE INVENTION

The present invention relates generally to the inactivation of viruses and more particularly to a method for inactivating non-enveloped viruses using a viricide-potentiating agent.

BACKGROUND OF THE INVENTION

The spread of infectious disease resulting from the transfusion of contaminated blood or from the administration of contaminated blood products (e.g., plasma, blood factors, etc.) has been well documented and is recognized as a major public health concern. Most notably, the transmission of viral hepatitis and Acquired Immune Deficiency Syndrome (AIDS) through contaminated blood and blood products has received widespread attention. It is to be noted, however, that viral hepatitis and AIDS are only two of the many diseases that can be spread through the use of contaminated blood and blood products. Lesser known pathogenic viruses, such as T-cell lymphotropic viruses (Types I and II), cytomegalovirus, Epstein-Barr virus and the paroviruses, may also be spread through contaminated blood and blood products. In addition, still other pathogenic viruses that have not yet even been identified or recognized as being pathogenic infectious agents may be transmitted through contaminated blood and blood products and, therefore, similarly pose a serious public health risk. The HIV virus is illustrative of a virus that, until recently, was not even recognized as a pathogenic virus. Less than two decades ago, AIDS was not a recognized disease; today, there are over 10 million people worldwide who have contracted AIDS, many of these people having contracted the disease through the use of infected blood or blood products. Thus, it is clear that there is a great need for a method for effectively inactivating blood-borne infectious viruses.

In response to the aforementioned need, a number of techniques have been devised for inactivating infectious viral agents in blood and/or blood products. A review of many of these techniques is presented in Suomela, "Inactivation of Viruses in Blood and Plasma Products," *Transfusion Medicine Reviews*, Vol. VII, No. 1, pp. 42–57 (January 1993), which is incorporated herein by reference.

One such technique which has been used to inactivate viruses in blood and/or blood products is pasteurization. See e.g., Burnouf-Radosevich et al., "A Pasteurized Therapeutic Plasma," *Infusionstherapie*, 19:91–94 (1992), which is incorporated herein by reference. The pasteurization of blood and/or blood components is most often effected by heating them in the liquid state for 10 hours at 60° C. A small amount of a protein stabilizer, such as caprylate or tryptophanate, is often added to the preparation. After pasteurization has been completed, the stabilizer typically must be removed from the preparation prior to its clinical use. As is the case with many of the viral inactivation techniques discussed herein, pasteurization is more effective in inactivating enveloped viruses (i.e., viruses having a lipid envelope surrounding the viral capsid) than in inactivating non-enveloped viruses (i.e., viruses which lack a lipid envelope surrounding the viral capsid).

Another technique which has been used to inactivate viruses in blood and/or blood products is the solvent/detergent (S/D) method. See e.g., Hellstern et al., "Manufacture and in vitro Characterization of a Solvent/Detergent-Treated Human Plasma," *Vox Sang*, 63:178–185 (1992); Horowitz et at., "Solvent/Detergent-Treated Plasma: A Virus-Inactivated Substitute for Fresh Frozen Plasma," *Blood*, 79(3):826–831 (Feb. 1, 1992); and Piquet et al., "Virus Inactivation of Fresh Frozen Plasma by a Solvent Detergent Procedure: Biological Results, *Vox Sang*, 63:251–256 (1992), all of which are incorporated herein by reference. The S/D method, which is limited too use in inactivating enveloped viruses, involves treating a blood preparation with an organic mixture which disrupts the lipid envelope of enveloped viruses. The disruption of the lipid envelope leads either to complete structural disruption of the virus or to destruction of the cell receptor recognition site on the virus. In either case, the virus is rendered noninfectious. The solvent used in the S/D method is most often tri-(n-butyl)phosphate (TNBP), and the detergent is either Tween 80, Triton X-100 or Na-cholate. Temperature and time influence the efficacy of the S/D method, typical temperatures being in the range of 24° C. to 37° C and the typical duration of treatment being at least 6 hours. As is the case with most additives used in viral inactivation techniques, the substances responsible for viral inactivation must be removed from the treated products before their clinical use.

Still another technique which has been used to inactivate viruses in blood and/or blood products is photochemical inactivation. See e.g., Mohr et al., "Virus Inactivated Single-Donor Fresh Plasma Preparations," *Infusiontherapie*, 19:79–83 (1992); Wagner et al., "Differential sensitivities of viruses in red cell suspensions to methylene blue photosensitization," *Transfusion*, 34(6) :521–526 (1994); Wagner et al., "Red cell alterations associated with virucidal methylene blue phototreatment," *Transfusion*, 33:30–36 (1993); Mohr et al., "No evidence for neoantigens in human plasma after photochemical virus inactivation," *Ann. Hematol*, 65:224–228 (1992); Lambrecht et al., "Photoinactivation of Viruses in Human Fresh Plasma by Phenothiazine Dyes in Combination with Visible Light," *Vox Sang*, 60:207–213 (1991), Goodrich et at., "Selective inactivation of viruses in the presence of human platelets: UV sensitization with psoralen derivatives, *Proc. Natl. Acad. Sci. USA*, 91:5552–5556(June 1994); *Virus Inactivation in Plasma products*, J.-J Morgenthaler, ed. Karger, N.Y. (1989); and *BioWorld Today*, Vol.4, No. 229, pages 1 and 4 (Nov. 24, 1993), all of which are incorporated herein by reference. The photochemical inactivation of a blood preparation typically involves treating the blood preparation with a photoactivatable chemical and then irradiating the preparation with light of a sufficient wavelength to activate the photoactivatable chemical. Examples of photoactivatable chemicals used in the photochemical inactivation of viruses present in blood preparations include psoralens, hypericin, methylene blue and toluidine blue. It is believed that psoralens, which have an affinity for nucleic acids, inactivate viruses by intercalating between viral nucleic acid base pairs and, in the presence of UVA light, forming a covalent bond with the viral nucleic acid, thereby preventing its transcription and/or replication. The manner in which hypericin, methylene blue and toluidine blue inactivate viruses is not as well-defined as that for psoralens. However, it is believed that these chemicals, when photoactivated, generate the highly reactive entity, singlet oxygen, which then attacks the cellular structure (e.g. viral envelope) of the virus.

Whereas photochemical inactivation has been largely successful in inactivating enveloped viruses, it has been largely unsuccessful in inactivating non-enveloped viruses. The failure of photochemical inactivation to inactivate non-enveloped viruses poses a significant public health problem since Poliovirus, Adenovirus, Hepatitis A and Parvovirus (Parvo B19) are among those non-enveloped viruses that are pathogenic to humans.

It should be noted that photochemical inactivation of the type described above has been most successful when applied to inactivating viruses in blood preparations lacking red blood cells (e.g., plasma). This is because blood preparations which include red blood cells typically absorb light at the same wavelengths used to photoactivate the chemicals.

Accordingly, there currently exists a need for a method for inactivating non-enveloped viruses, as well as enveloped viruses, in whole blood and/or blood products (e.g., plasma, platelets, blood factors, etc.).

SUMMARY OF THE INVENTION

It is an object of the present invention to provide a novel method for inactivating viruses.

It is another object of the present invention to provide a method as described above which can be used to inactivate non-enveloped viruses, as well as enveloped viruses.

It is yet another object of the present invention to provide a method as described above which can be used to inactivate both enveloped viruses and non-enveloped viruses present in whole blood and/or blood products.

It is still another object of the present invention to provide a method as described above in which existing viricides may be used.

According to one aspect of the invention, there is provided a method for inactivating a virus, the method comprising the steps of (a) administering a viricide to the virus; and (b) administering a chemical agent to the virus that enhances the efficacy of the viricide against the virus. In a preferred embodiment, the viricide is a photoactivatable viral inactivating agent, such as a psoralen, hypericin, methylene blue, toluidine blue or the like, and the chemical agent enhances the efficacy of the viricide against the virus by physically transforming the virus so that the lipid concentration in or at least partially surrounding the viral capsid of the virus is increased. Without wishing to be limited by any particular theory of the invention, the present inventors believe that this increase in the lipid concentration in or at least partially surrounding the viral capsid increases the efficacy of the viricide, where the viricide is a psoralen or a similar acting viricide, by causing the virus to more efficiently sequester or take up the hydrophobic viricide or, where the viricide is methylene blue or a similar acting viricide, by increasing the half-life of singlet oxygen or a similar reactive entity in the area of the interface between the virus and its aqueous environment.

Preferably, the aforementioned viricide-potentiating chemical agent includes a first moiety and a second moiety, the first moiety having an affinity for a component of the virus and the second moiety comprising a lipid tail, the first moiety and the second moiety being structurally interrelated in such a way that, when the first moiety becomes associated with a component of the virus, the second moiety penetrates or at least partially surrounds the viral capsid of the virus. The first moiety may be a moiety having an affinity for nucleic acid, such as a nucleic acid probe, a psoralen, an acridine, a cationic amine or the like. Examples of cationic amines suitable for use in the present invention include dioctadecylamidoglycylspermine, N-[1-(2,3-dioleoyloxy)propyl]-N,N,N-trimethylammonium methylsulfate and 2,3-dioleyloxy-N-[2(sperminecarboxamido)ethyl]-N,N-dimethyl-1-propanaminium trifluoroacetate.

In accordance with the teachings of the present invention, the above-mentioned photoactivatable viricide may be activated in the conventional manner using light of an appropriate activating wavelength.

According to another aspect of the invention, there is provided a method for inactivating a non-enveloped virus present in a sample of whole blood or a blood product, the method comprising the steps of (a) administering a viricide to the sample; and (b) administering a viricide-potentiating chemical agent to the sample that enhances the efficacy of the viricide against the non-enveloped virus. In a preferred embodiment, the viricide is a photoactivatable drug, such as a psoralen, hypericin, methylene blue or toluidine blue, and the viricide-potentiating chemical agent is of the type described above. The viricide and the viricide-potentiating chemical agent may be added to the whole blood or blood product sample simultaneously or sequentially, the chemical agent preferably being added to the blood sample prior to the addition of the viricide. If photoactivation of the aforementioned photoactivatable viricides is employed, the blood sample is preferably devoid of red blood cells or other agents which may absorb light of the viricide-activating wavelength. If the blood sample contains plasma proteins and a cationic amine of the type described above is used is the viricide-potentiating chemical agent, a citrate or a similar compound may be added to the blood sample to inhibit the coagulation of plasma proteins by the cationic amine.

According to still another aspect of the invention, there is provided a method for increasing the susceptibility of a non-enveloped virus to a viricide, the method comprising the step of administering to the non-enveloped virus a viricide-potentiating chemical agent that increases the efficacy of the viricide against the non-enveloped virus. In a preferred embodiment, the viricide is a photoactivatable drug of the type described above, and the viricide-potentiating chemical agent is of the type described above. Where the photoactivatable viricide is activated using light, the non-enveloped virus is preferably present in a medium devoid of agents that absorb light of the viricide-activating wavelength.

Additional objects, aspects, features and advantages, of the present invention will be set forth in part in the description of preferred embodiments which follows, and in part will be obvious from the description of preferred embodiments or may be learned by practice of the invention. The preferred embodiments will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings.

DETAILED DESCRIPTION OF PREFERRED EMBODIMENTS

As noted above, many of the techniques presently used to inactivate viruses in whole blood and/or blood products are substantially less effective in inactivating non-enveloped viruses than in inactivating enveloped viruses. Without being limited by theory, the present inventors believe that this differential in the efficacy of certain viricides against enveloped and non-enveloped viruses is attributable, in large part, to the presence or absence of a lipid envelope surrounding the viral capsid of the virus. For example, the present inventors believe that enveloped viruses are more susceptible than non-enveloped viruses to the effects of photoactivatable viricides, such as psoralens, hypericin, methylene blue, toluidine blue or the like, because (1) these viricides are hydrophobic and/or generate highly reactive agents like singlet oxygen which have an extremely short half-life in an aqueous solution, such as blood; and (2) the lipid envelope of enveloped viruses is similarly hydrophobic and, therefore, permits the rapid sequestration of such viricides from an aqueous solution and/or increases the lifetime of the aforementioned short-lived reactive agents.

Although not wishing to be limited by any particular theory of the invention, the present inventors consequently reasoned that one way in which to increase the sensitivity of non-enveloped viruses to viral inactivation technologies successful against enveloped viruses is to physically transform non-enveloped viruses so that they behave more like enveloped viruses. In accordance with a preferred embodiment of the present invention, this is accomplished by treating a non-enveloped virus with a viricide-potentiating chemical agent which increases the hydrophobicity of either the viral capsid or at least a portion of the environment surrounding the viral capsid of the non-enveloped virus. Preferably, the viricide-potentiating chemical agent comprises a first moiety having an affinity for a component of the virus and a second moiety which includes a hydrophobic moiety. The first and second moieties are preferably structurally interrelated in such a way that, when the first moiety becomes associated with a component of the virus, the second moiety penetrates or surrounds at least a portion of the viral capsid of the virus, thereby rendering the-non-enveloped virus susceptible to the many of the same viral inactivation techniques which are successful against enveloped viruses. The first moiety may be a psoralen, acridine, polyamine, nucleic acid probe or similar molecule having an affinity for nucleic acids. See Anderson et at., "Psoralen Photochemotherapy of Cutaneous Disorders," *Ann. Rev. Pharmacol. Toxicol,* 20:235–257 (1980); Asseline et al., "Nucleic acid-binding molecules with high affinity and base sequence specificity: Intercalating agents covalently linked to oligodeoxynucleotides, *Proc. Natl. Acad. Sci. USA,* 81:3297–3301 (1984), and Letsinger et al., "Cholesteryl-conjugated oligonucleotides: Synthesis, properties, and activity as inhibitors of replication of human immunodeficiency virus in cell culture, *Proc. Natl. Acad. Sci. USA,* 86:6553–6556 (1989); Barthel et al., "Laboratory Methods: Gene Transfer Optimization with Lipospermine-coated DNA, DNA and *Cell Biology,* 12:553–560 (1993); Loeffler et al., "Lipopolyamine-Mediated Transfection. Allows Gene Expression Studies in Primary Neuronal Cells, *J. of Neurochemistry,* 54:1812–1815 (1990); Neumann et al., *Biotechniques,* 12:643 et seq. (1987); and Hawley-Nelson et at., *Focus,* 15:3 (1993), all of which are incorporated herein by reference. Because blood platelets, erythrocytes and plasma proteins do not contain genomic nucleic acids, compounds that specifically target nucleic acids will desirably result in the targeting of viruses. (White blood cells do contain nucleic acids and, therefore, will also be targeted by these viricides; however, because many of these white blood cells are infected with unwanted viruses and because white blood cells are typically filtered from blood products anyway before being administered to patients, the targeting of white blood cells by such viricides will not be undesirable.)

Instead of being a moiety which targets nucleic acids, the first moiety may be an antibody or similar molecule having an affinity for a viral capsid protein or the like.

The second moiety preferably comprises a lipid tail or a similarly hydrophobic entity. The first and second moieties of the viricide-potentiating chemical agent are preferably structurally interrelated so that, when the first moiety becomes associated with its corresponding component of the virus, the second moiety at least partially surrounds the viral capsid of the virus. The cumulative effect of many molecules of the viricide-potentiating chemical agent acting against a single non-enveloped virus is preferably to simulate an envelope surrounding the viral capsid of the non-enveloped virus. It should be understood, however, that it is not necessary for a complete envelope to be formed around the viral capsid for the viricide-potentiating effects of the present invention to be felt. In fact, the present inventors believe that the viricide-potentiating effects of the present invention will be experienced even if the hydrophobic second moiety is not disposed outside of the viral capsid, but rather is disposed within the viral capsid, itself, perhaps forming a hydrophobic channel or the like.

Examples of the viricide-potentiating chemical agent of the present invention include cationic lipopolyamines, such as dioctadecylamidoglycylspermine (commercially available from BioSepra, Inc., Marlborough, Mass. under the trademark TRANSFECTAM®), the polycationic lipid 2,3-dioleyloxy-N-[2(sperminecarboxamido)ethyl]-N,N-dimethyl-1-propanaminium trifluoroacetate (which is commercially available from Life Technologies, Inc., Gaithersburg, Md. in the form of a liposomal formulation under the trademark LipofectAMINE™), N-[1-(2,3-dioleoyloxy)propyl]-N,N,N-trimethylammonium methyl-sulfate (which is commercially available from Boehringer Mannheim GmbH, Germany in the form of a liposomal formulation), as well as similar DNA transfection agents. Other examples of the viricide-potentiating chemical agent of the present invention may include lipid-derivatized acridines, such as 2-methoxy-6-chloro-9-octadecylaminoacridine or the compound represented below by reference numeral I.

(I)

X = 5–6

To inactivate a quantity of enveloped and non-enveloped viruses present within a sample of whole blood or a blood product in accordance with the teachings of the present invention, one adds appropriate amounts of a viricide and a viricide-potentiating chemical agent to the blood sample and, in those instances in which the viricide needs to be activated, activates the viricide. In a preferred embodiment, the viricide is a photoactivatable viral inactivating agent, such as a psoralen, hypericin, methylene blue, toluidine blue, the like, and the viricide-potentiating chemical agent is as described above. The aforementioned photoactivatable viral inactivating agent may be photoactivated, in the conventional manner, or may be chemically activated, in the manner described in commonly-assigned, presently-pending U.S. patent application Ser. No. 08/179,437, filed Jan. 10, 1994, which is incorporated herein by reference. Alternative viricides which may be used in the method of the present invention are described in U.S. Ser. No. 08/179,437.

Preferably, the viricide-potentiating chemical agent is added to the blood sample prior to the addition of the viricide to the blood sample; however, this is not required. The concentration of viricide preferably added to the blood sample is that which is ordinarily used to inactivate enveloped viruses (e.g., 1 µM methylene blue). The concentration of viricide-potentiating chemical agent preferably added to the blood sample is that which renders non-enveloped viruses susceptible to the viricide added at the concentration indicated above. If the blood sample contains plasma proteins and a cationic amine of the type described above is used as the viricide-potentiating chemical agent, a citrate or a similar compound may be added to the blood sample to inhibit the coagulation of plasma proteins by the cationic amine.

The following examples are illustrative only and should in no way limit the scope of the present invention.

EXAMPLE 1

One mg of TRANSFECTAM® DNA transfection agent (dioctadecylamidoglycylspermine commercially available from BioSepra, Inc., Marlborough, Mass.) was dissolved in 400 µl of anhydrous ethanol. A 1 µl volume of the aforementioned TRANSFECTAM®:ethanol mixture was then added to a first set of three 19 µl volumes of T4 virus stock suspension. (T4 is a non-enveloped virus.) A 2.5 µl volume of the TRANSFECTAM®:ethanol mixture was then added to a second set of three 19 µl volumes of T4 virus stock suspension. A third set of three 19 µl volumes of T4 virus stock suspension to which a sample of ethanol lacking TRANSFECTAM® was added served as a control.

A 1 µl volume of methylene blue at a concentration of 0.025 mg/ml was then added to one of the three tubes from each of the above-described 0 µl, 1 µl and 2.5 µl sets. Next, a 1 µl volume of methylene blue at a concentration of 0.0025 mg/ml was added to another of the three tubes from each of the above-described 0 µl, 1 µl and 2.5 µl sets. A 1 µl volume of methylene blue at a concentration of 0.00025 mg/ml was then added to the remaining three tubes. The suspensions were incubated under the radiation of a sodium vapor lamp for 30 minutes prior to dilution and spotting onto three soft agar overlays containing the host bacterium. The first plate was spotted with the three 0 µl TRANSFECTAM® suspensions at methylene blue concentrations of 0.025 mg/ml, 0.0025 mg/ml and 0.00025 mg/ml, the second plate was spotted with the three 1 µl TRANSFECTAM® suspensions at methylene blue concentrations of 0.025 mg/ml, 0.0025 mg/ml and 0.00025 mg/ml, and the third plate was spotted with the three 2.5 µl TRANSFECTAM® suspensions at methylene blue concentrations of 0.025 mg/ml, 0.0025 mg/ml and 0.00025 mg/ml, as well as with a control T4 suspension containing 2.5 µl TRANSFECTAM® and 0 mg/ml methylene blue. After overnight incubation, the plates were photographed, the photographs of the three plates being shown in FIGS. 1 through 3, respectively. (Reference numerals –3, –4 and –5 represent corresponding sets of viral suspensions subjected to methylene blue concentrations of 0.025 mg/ml, 0.0025 mg/ml and 0.00025 mg/ml, respectively.)

Figure 1:
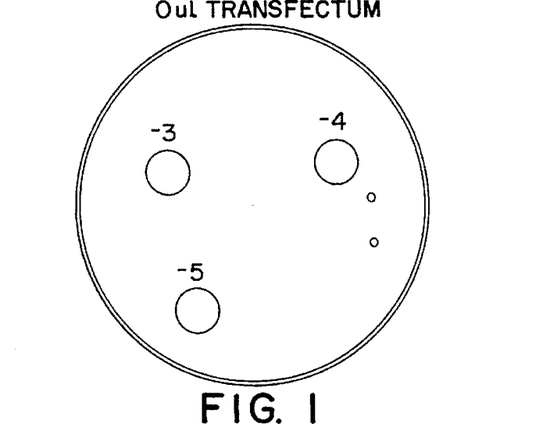
FIG. 1 is a photograph of a bacterial host plate onto which T4 viral suspensions containing 0 µl of TRANSFECTAM® and methylene blue concentrations of 0.025 mg/ml, 0.0025 mg/ml and 0.00025 mg/ml were spotted and allowed to incubate overnight in accordance with Example 1.
Figure 2:
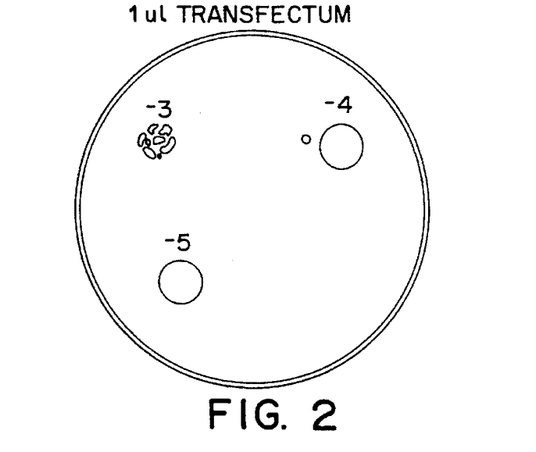
FIG. 2 is a photograph of a bacterial host plate onto which T4 viral suspensions containing 1 µl of TRANSFECTAM® and methylene blue concentrations of 0.025 mg/ml, 0.0025 mg/ml and 0.00025 mg/ml were spotted and allowed to incubate overnight in accordance with Example 1.
Figure 3:
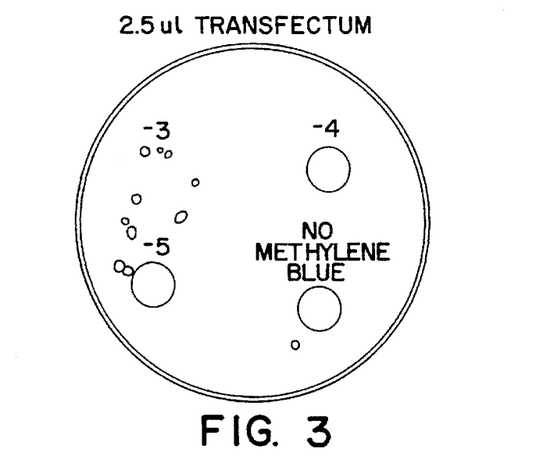
FIG. 3 is a photograph of a bacterial host plate onto which T4 viral suspensions containing 2.5 μl of TRANS-FECTAM® and methylene blue concentrations of 0 mg/ml, 0.025 mg/ml, 0.0025 mg/ml and 0.00025 mg/ml were spotted and allowed to incubate overnight in accordance with Example 1.

A comparison of the plates of FIGS. 1 through 3, more particularly a comparison of the members of set –3 in FIGS. 1 through 3, quite clearly illustrates the potentiating effect of TRANSFECTAM® on methylene blue. Referring first to FIG. 1, it can be seen that, in the absence of TRANSFECTAM®, T4 was not killed by photoactivated methylene blue. By comparison, in FIGS. 2 and 3, the killing effect of methylene blue on T4 is readily apparent, the effect being more pronounced in FIG. 3 where a greater quantity of TRANSFECTAM® was added.

It should be noted that TRANSFECTAM®, in the absence of methylene blue, did not kill the virus (see FIG. 3).

EXAMPLE 2

1 mg of TRANSFECTAM® was dissolved into 40 µl of anhydrous ethanol and was then further diluted into 360 µl of sterile distilled water. 1 µl of the aforementioned TRANSFECTAM® solution was then added to each of a series of eight 1.5 ml microfuge tubes each containing 17.5 µl of T4 virus stock suspension. 1 µl of an ethanol water solution lacking TRANSFECTAM® was added to each of another series of eight 1.5 ml microfuge tubes each containing 17.5 µl of T4 virus stock suspension. All of the samples were incubated at room temperature for 60 minutes.

A methylene blue stock solution (25 mg/ml) prepared in ethanol:phosphate buffered saline, pH 7.4 (1:2), was diluted 1:100, 3:500, 1:500, 1:1000, 3:5000, 1:5000 and 1:10,000 in ethanol:phosphate buffered saline. 1 µl of each dilution, as well as a control containing no methylene blue, was added to a virus suspension containing TRANSFECTAM® and to a corresponding suspension lacking TRANSFECTAM®. One of the suspensions with TRANSFECTAM® and one without were treated with 1 µl of ethanol:phosphate buffered saline. The viral suspensions were then all incubated under the radiation from a sodium vapor lamp (70 W) for 60 min. The viral suspensions were then each diluted into dilution broth consisting of Bacto tryptone (10 g/l) and sodium chloride (5 g/l), pH 7.2, before mixing with host cells (E. coli strain 92-055V) in liquified soft agar. The soft agar consisted of Difco minimal agar (6.5 g/l), Bacto tryptone (13.0 g/l), sodium chloride (8.0 g/l), sodium citrate, dihydrate (2.0 g/l) and glucose (3.0 g/l). The dilution broth and media formulations are described in *Experiments in Molecular Genetics, Miller,* 1977, Cold Spring Harbor Laboratory, Cold Spring Harbor, N.Y., which is incorporated herein by reference. The soft agar suspensions were then overlaid onto bottom agar and incubated overnight at 37° C. The bottom agar was identical to the soft agar, except that the agar concentration was 10 g/l arid the glucose concentration was 1.3 g/l. The plaques were then counted the following day, and viable virus determined (expressed as plaque forming units, PFU). The results are expressed below in Table I.

TABLE I

| Methylene Blue Dilution | Transfectam Present | PFU |
| --- | --- | --- |
| 1:100 | no | $<10^3$ |
| 1:100 | yes | less than 1000 $<10^3$ |
| 3:500 | no | $3 \times 10^3$ 3000 |
| 3:500 | yes | $<10^3$ 1000 |
| 1:500 | no | $50 \times 10^5$ 5,000,000 |
| 1:500 | yes | $36 \times 10^4$ 360,000 |
| 1:1000 | no | $95 \times 10^6$ |
| 1:1000 | yes | $21 \times 10^5$ |
| 3:5000 | no | $21 \times 10^7$ |
| 3:5000 | yes | $10 \times 10^7$ |
| 1:5000 | no | $30 \times 10^7$ |
| 1:5000 | yes | $18 \times 10^7$ |
| 1:10,000 | no | $39 \times 10^8$ |
| 1:10,000 | yes | $23 \times 10^8$ |
| no methylene blue | no | $29 \times 10^8$ |
| no methylene blue | yes | $32 \times 10^8$ |

The above data demonstrate that TRANSFECTAM® (0.125 mg/ml) enhances the viricidal effect of methylene blue. At certain conditions, almost a 1.5 log greater reduction in viable virus is seen in the presence of TRANSFECTAM® than in its absence. The effect of TRANSFECTAM® is most clearly seen as the concentration of methylene blue was decreased to the dilutions of 3:500, 1:500 and 1:1000. At higher concentrations of methylene blue, the virus was killed, even in the absence of TRANSFECTAM®, and at lower concentrations of methylene blue, the virus was not killed, even in the presence of TRANSFECTAM®.

EXAMPLE 3

1 mg of TRANSFECTAM® was dissolved in 40 µl of anhydrous ethanol, and 2.5 µl of this solution was distributed to each of seven microfuge tubes each containing 17.5 µl of T4 virus. A series of eight control tubes each containing T4 were treated with 2.5 µl of anhydrous ethanol. After 2 hours of incubation at room temperature, methylene blue stock solutions at the below-indicated concentrations were added in 1 µl volumes to the tubes, and the samples were incubated under the radiation from a sodium vapor lamp for 1 hour. The samples were then diluted and PFU's determined. The results are summarized below in TABLE II.

TABLE II

| Methylene Blue Concentration (mg/ml) | Transfectam Present | PFU |
| --- | --- | --- |
| 0.75 | no | $<10^3$ |
| 0.75 | yes | $<10^3$ |
| 0.25 | no | $15 \times 10^3$ |
| 0.25 | yes | $<10^3$ |
| 0.125 | no | $10 \times 10^4$ 100 × 10³ |

TABLE II-continued

| Methylene Blue Concentration (mg/ml) | Transfectam Present | PFU |
| --- | --- | --- |
| 0.125 | yes | $<10^3$ |
| 0.075 | no | $10 \times 10^5$ 1000 × 10³ |
| 0.075 | yes | $<10^3$ |
| 0.025 | no | $18 \times 10^7$ |
| 0.025 | yes | $14 \times 10^5$ |
| 0.0125 | no | $21 \times 10^7$ |
| 0.0125 | yes | $20 \times 10^6$ |
| 0.0 | no | $35 \times 10^7$ |
| 0.0 | yes | $6 \times 10^7$ |

The data in Table II indicate that an even greater enhancement of the viricidal effects of irradiated methylene blue was observed at a higher concentration of TRANSFECTAM® (3.125 mg/ml) than was observed under the conditions of Example 2. The data of TABLE II indicate that, generally speaking, over a 2 log greater reduction in viable non-enveloped virus was observed when TRANSFECTAM® was included in the reaction mixture than when it was omitted.

EXAMPLE 4

A first series of eight microcentrifuge robes each containing 19 µl of T4 virus stock solution were treated with 2.5 µl of TRANSFECTAM®, and a second series of eight microcentrifuge tubes each containing 19 µl of T4 virus stock solution were treated with 2.5 µl of a 2 mg/ml stock solution of LipofectAMINE™ (a liposomal formulation of a polycationic lipid described above in greater detail). After 2 hours at room temperature, 1 µl of various dilutions of methylene blue stock solutions (see TABLE III below) were added to the tubes, and the samples were incubated under the radiation of a sodium vapor lamp for 1 hour. The samples were then diluted and plated for PFU's. The results are shown below in TABLE-III.

TABLE III

| Methylene Blue Concentration (mg/ml) | Additive | PFU |
| --- | --- | --- |
| 1.25 | LipofectAMINE | $<10^3$ |
| 1.25 | TRANSFECTAM | $<10^3$ |
| 0.75 | LipofectAMINE | $<10^3$ |
| 0.75 | TRANSFECTAM | $<10^3$ |
| 0.25 | LipofectAMINE | $<10^3$ |
| 0.25 | TRANSFECTAM | $<10^3$ |
| 0.125 | LipofectAMINE | $<10^3$ |
| 0.125 | TRANSFECTAM | $<10^3$ |
| 0.075 | LipofectAMINE | $24 \times 10^4$ |
| 0.075 | TRANSFECTAM | $39 \times 10^3$ |
| 0.025 | LipofectAMINE | $53 \times 10^5$ |
| 0.025 | TRANSFECTAM | $15 \times 10^5$ |
| 0.0125 | LipofectAMINE | $50 \times 10^5$ |
| 0.0125 | TRANSFECTAM | $61 \times 10^5$ |
| 0.0 | LipofectAMINE | $20 \times 10^9$ |
| 0.0 | TRANSFECTAM | $11 \times 10^9$ |

The data in TABLE III indicate that LipofectAMINE™ and TRANSFECTAM® appear to be comparable in their viricide-potentiating capacities.

EXAMPLE 5

2-methoxy-6-chloro-9-octadecylaminoacridine (a "tailed quinacrine") was synthesized as follows:

A 200 mL round bottom flask was charged with phenol (25 gm), 2-methoxy-6,9-dichloroacridine (5.56 gm, 2×10$^{-2}$ moles) and octadecylamine (5.40 gm, 2×10$^{-2}$ moles). The mixture was heated in an oil bath to 100° C. to provide a yellow solution. The solution was stirred by means of a magnetic stir bar for one hour. After cooling, the reaction mixture was stirred in 500 mL of water containing 25 gm of 50% aqueous sodium hydroxide. The precipitated oil was dissolved in 400 mL of ethyl acetate and the organic solution was washed twice with 100 mL portions of 5% aqueous sodium hydroxide solution. After drying over magnesium sulfate, the organic solution was filtered and evaporated under vacuum. The resulting yellow oil solidified on standing. The solid product was recrystallized from 400 mL of methanol to give 8.7 gm (85%) of the desired product as a yellow powder melting at 64–65° C.

EXAMPLE 6

The tailed quinacrine synthesized in Example 5 was prepared at 2.5 mg/ml in anhydrous ethanol. 2.5 µl of this stock solution was added to each of a series of seven microfuge tubes each containing 16.5 µl of T4 virus. A corresponding series of seven microfuge tubes each containing 16.5 µl of T4 virus received ethanol without the tailed quinacrine. After incubation at room temperature for 1 hour, methylene blue was added to the tubes in the dilutions indicated below, the tubes were irradiated and PFU's were determined in the same manner as in Example 2. The results are shown below in TABLE IV.

TABLE IV

| Methylene Blue Dilution | Tailed Quinacrine Present | PFU |
|---|---|---|
| 3:500 | no | <10$^3$ |
| 3:500 | yes | 11 × 10$^3$ |
| 1:500 | no | 14 × 10$^5$ |
| 1:500 | yes | 24 × 10$^4$ |
| 1:1000 | no | 47 × 10$^6$ |
| 1:1000 | yes | 26 × 10$^6$ |
| 3:5000 | no | 30 × 10$^6$ |
| 3:5000 | yes | 16 × 10$^6$ |
| 1:5000 | no | 30 × 10$^8$ |
| 1:5000 | yes | 18 × 10$^8$ |
| 1:10,000 | no | 47 × 10$^8$ |
| 1:10,000 | yes | 19 × 10$^8$ |
| control | no | 87 × 10$^8$ |
| control | yes | 75 × 10$^8$ |

The data in TABLE IV indicate that only a slight enhancement of virus killing was observed with the addition of the tailed quinacrine. Clearly, this particular compound is not as effective as the cationic lipopolyamines. However, it should be recognized that alteration of the lipid tail or the utilization of a different acridine could greatly improve the efficacy of this type of compound.

EXAMPLE 7

10 µl of freshly prepared blood plasma, 1.5 µl of sodium citrate stock (to give a final concentration of 129 mM in the mixture), 2.5 µl of TRANSFECTAM® stock (to give a final concentration of 125 µg/ml in the mixture), 1 µl of methylene blue stock (to give the final concentrations listed below) and 5.0 µl of T4 virus stock were added to a series of eight tubes. A control series was prepared in the identical fashion, except that TRANSFECTAM® was omitted. Sodium citrate was added to the mixtures to inhibit plasma coagulation, some of which was observed in the absence of sodium citrate. With the addition of sodium citrate, coagulation was not observed. After incubation for 1 hour at room temperature and under room lighting, the samples were irradiated with radiation from a sodium vapor lamp for 1 hour and then diluted, mixed with host cells, and plated for PFU determination. The results are shown below in TABLE V.

TABLE V

| Methylene Blue Concentration | PFU, Without TRANSFECTAM | PFU, With TRANSFECTAM |
|---|---|---|
| 12.5 µg/ml | <10$^3$ | <10$^3$ |
| 7.5 µg/ml | <10$^3$ | <10$^3$ |
| 2.5 µg/ml | <10$^3$ | <10$^3$ |
| 1.25 µg/ml | 13 × 10$^3$ | 42 × 10$^3$ |
| 0.75 µg/ml | 12 × 10$^6$ | 25 × 10$^5$ |
| 0.25 µg/ml | 12 × 10$^6$ | 42 × 10$^5$ |
| 0.125 µg/ml | 16 × 10$^7$ | 20 × 10$^7$ |
| 0 µg/ml | 24 × 10$^8$ | 33 × 10$^8$ |

As can be seen, at methylene blue concentrations of 1.25 µg/ml and 0.75 µg/ml, TRANSFECTAM® enhanced viral inactivation in plasma, albeit not to the same extent as was observed in buffer solutions.

EXAMPLE 8

A second "tailed" nucleic acid intercalator was synthesized as follows:

First, 5.56 gm (0.02 moles) of 6,9-dichloro-2-methoxyacridine and 80 gm (approximately 0.2 moles) of Jeffamine D400 (an oligomeric diaminooligopropylene oxide available from Aldrich Chemical Company or Huntsman Corporation of Austin, Tex.) were added to a 250 mL, round bottom flask. A magnetic stir bar was placed in the flask, and the contents were stirred and heated in an oil bath set at 150° C. After four hours, an aliquot of the orange solution was taken and examined by TLC (silica, 5% methanol in methylene chloride) and was found to be absent of the starting acridine. The cooled reaction mixture was poured into 500 mL of water, stirred and then allowed to settle. The oily product was isolated by decantation of the aqueous supernatant. The product was washed three more times by decantation with 300 mL portions of water. The resulting orange oil was dissolved in 250 mL of methylene chloride and this solution was washed once with 250 mL of water. After drying over magnesium sulfate, the solution was filtered and the stripped under vacuum. Yield of product as an orange oil was 10.5 gm (82%).

Next, 640 mg (approximately $1\times10^{-3}$ moles) of the amino-oligopropyleneoxyacridine and 351 mg ($1\times10^{-3}$ moles) of 2-octadecen-1-yl anhydride were dissolved in 1.0 mL of methylene chloride and placed in an oil bath set at 100° C. The methylene chloride was allowed to evaporate and the clear yellow residue was kept at 100° C. for 2 minutes. A this point, TLC (silica, 5% methanol in methylene chloride showed clean conversion to product (rF, amino-oligopropylene oxyacridine=0.13; rF, product=0.64). The oily product was chromatographed on silica using 5% methanol in methylene chloride as eluent. After evaporation of solvent, yield of product as a sticky yellow oil was 900 mg.

EXAMPLE 9

A "tailed" acridine was synthesized in the manner discussed in Example 8, and a stock solution thereof (100 mg/ml) was prepared in ethanol. Methylene blue stock solutions were prepared in etoh:pbs (1:2) such that the addition of 1 µl there of to the incubation mixtures hereinafter described gave the final concentrations indicated below. The incubation mixtures included 16.5 µl of T4 virus stock and 2.5 µl of the "tailed" acridine stock, as well as 1.0 of methylene blue stock of the appropriate dilution. A series of controls were prepared by substituting 2.5 µl of etoh:pbs for the "tailed" acridine. The samples were irradiated under a sodium vapor lamp for 1 hour, diluted, and then plated for PFU's. The results are shown below in TABLE VI.

TABLE VI

| Methylene Blue Concentration | PFU, Without "Tailed" Acridine | PFU, With "Tailed" Acridine |
| --- | --- | --- |
| 12.5 µg/ml | $<10^3$ | $<10^3$ |
| 7.5 µg/ml | $<10^3$ | $<10^3$ |
| 2.5 µg/ml | $1 \times 10^4$ | $<10^3$ |
| 1.25 µg/ml | $7 \times 10^4$ | $5 \times 10^3$ |
| 0.75 µg/ml | $5 \times 10^6$ | $16 \times 10^6$ |
| 0.25 µg/ml | $38 \times 10^7$ | $19 \times 10^6$ |
| 0.125 µg/ml | $19 \times 10^8$ | $19 \times 10^8$ |
| 0 µg/ml | $140 \times 10^8$ | $65 \times 10^8$ |

As can be seen, the "tailed" acridine of the present example appeared to exhibit improved efficacy as compared to the "tailed" acridine of Example 6. The present compound also possesses the property of being capable of dispersing well in aqueous media.

The embodiments of the present invention described above are intended to be merely exemplary and those skilled in the art shall be able to make numerous variations and modifications to them without departing from the spirit of the present invention. All such variations and modifications are intended to be within the scope of the present invention as defined in the appended claims.

What is claimed is:

1. A method for inactivating a non-enveloped virus, the non-enveloped virus having a viral capsid, said method comprising the steps of:

(a) administering a photoactivatable viricide to the non-enveloped virus; and (b) administering a viricide-potentiating chemical agent to the non-enveloped virus in a concentration that enhances the efficacy of the photoactivatable viricide against the non-enveloped virus, said viricide-potentiating chemical agent being selected from the group consisting of cationic lipopolyamines, 2-methoxy-6-chloro-9-octadecylaminoacridine and the following compound;

wherein x=5–6; and (c) activating said photoactivatable virucide.

2. The method as claimed in claim 1 wherein said viricide-potentiating chemical agent is a cationic lipopolyamine.

3. The method as claimed in claim 2 wherein said viricide-potentiating chemical agent is dioctadecylamidoglycylspermine.

4. The method as claimed in claim 1 wherein said viricide-potentiating chemical agent is selected from the group consisting of dioctadecylamidoglycylspermine, N-[1-(2,3-dioleoyloxy)propyl]-N,N,N-trimethylammonium methylsulfate and 2,3-dioleyloxy-N-[2-(sperminecarboxamido)ethyl]-N,N,dimethyl-1-propanaminium trifluoroacetate.

5. The method as claimed in claim 1 wherein said viricide-potentiating chemical agent is selected from the group consisting of 2-methoxy-6-chloro-9-octadecylaminoacridine and the following compound:

$$\text{HNCHCH}_2[\text{OCH}_2\text{CH}]_x\text{-NH} - \text{acridine structure with CH}_3, \text{CH}_3, \text{OCH}_3, \text{Cl, and } (CH_2)_{13}CH_3, \text{COOH side chain}$$

wherein x=5–6.

6. A method of increasing the susceptibility of a non-enveloped virus to a photoactivatable viricide, the non-enveloped virus having a viral capsid, said method comprising the step of administering to the non-enveloped virus a viricide-potentiating chemical agent in a concentration that increases the efficacy of the photoactivatable viricide against the non-enveloped virus, said viricide-potentiating chemical agent being selected from the group consisting of cationic lipopolyamines, 2-methoxy-6-chloro-9-octadecylaminoacridine and the following compound;

$$\text{(same structure as above)}$$

wherein x=5–6.

7. The method as claimed in claim 6 wherein said viricide-potentiating chemical agent is a cationic lipopolyamine.

8. The method as claimed in claim 7 wherein said viricide-potentiating chemical agent is dioctadecylamidoglycylspermine.

9. The method as claimed in claim 6 wherein said viricide-potentiating chemical agent is selected from the group consisting of dioctadecylamidoglycylspermine, N-[1-(2,3-dioleoyloxy)propyl]-N,N,N-trimethylammonium methylsulfate and 2,3-dioleyloxy-N-[2 (sperminecarboxamido)ethyl]-N,N-dimethyl-1-propanaminium trifluoroacetate.

10. The method as claimed in claim 6 wherein said chemical agent is selected from the group consisting of 2-methoxy-6-chloro-9-octadecylaminoacridine and the following compound:

$$\text{(same structure as above)}$$

wherein x=5–6.

11. A method for inactivating a non-enveloped virus in a sample, the non-enveloped virus having a viral capsid, the sample consisting essentially of at least one of blood plasma, red blood cells and platelets, said method comprising the steps of:

(a) adding a photoactivatable viricide to the sample, said viricide being a phenothiazine compound;

(b) adding a viricide-potentiating chemical agent to the sample in a concentration that enhances the efficacy of the photoactivatable viricide against the non-enveloped virus, said viricide-potentiating chemical agent being selected from the group consisting of cationic lipopolyamines, 2-methoxy-6-chloro-9-octadecylaminoacridine and the following compound $$\text{(same structure as above)}$$

wherein x=5–6; and (c) activating said photoactivatable viricide.

12. The method as claimed in claim 11 wherein said phenothiazine compound is selected from the group consisting of methylene blue and toluidine blue.

13. A method for inactivating a non-enveloped virus, the non-enveloped virus having a viral capsid, said method comprising the steps of:

(a) adding a photoactivatable viricide to the non-enveloped virus, said photoactivatable viricide being selected from the group consisting or psoralens, hypericin and phenothiazines;

(b) adding a viricide-potentiating chemical agent to the non-enveloped virus in a concentration that enhances the efficacy of the photoactivatable viricide against the non-enveloped virus, said viricide-potentiating chemical agent being selected from the group consisting of cationic lipopolyamines, 2-methoxy-6-chloro-9-octadecylaminoacridine and the following compound:

$$\text{(same structure as above)}$$

wherein x=5–6; and (c) activating said photoactivatable viricide.

14. The method as claimed in claim 13 wherein said activating step comprises photoactivating said photoactivatable viricide.

15. The method as claimed in claim 13 wherein the non-enveloped virus is present in a sample of whole blood or a blood product.

16. The method as claimed in claim 15 wherein said sample is substantially devoid of red blood cells.

17. The method as claimed in claim 15 wherein said adding steps are performed simultaneously.

18. The method as claimed in claim 15 wherein said adding steps are performed sequentially.

19. The method as claimed in claim 18 wherein said viricide-potentiating chemical agent is added prior to the addition of said photoactivatable viricide.

* * * * *